United States Patent [19]

Miyazawa et al.

[11] Patent Number: 4,969,953
[45] Date of Patent: Nov. 13, 1990

[54] ALCOHOL MIXTURE FOR PLASTICIZER AND METHOD FOR PRODUCING THE SAME

[75] Inventors: Chihiro Miyazawa; Akio Tsuboi, both of Kurashiki, Japan

[73] Assignee: Mitsubishi Kasei Corporation, Tokyo, Japan

[21] Appl. No.: 423,986

[22] Filed: Oct. 19, 1989

[30] Foreign Application Priority Data

Oct. 25, 1988 [JP] Japan .............................. 63-268772
Oct. 27, 1988 [JP] Japan .............................. 63-271396

[51] Int. Cl.$^5$ ................................................. C08K 5/05
[52] U.S. Cl. ................................. 106/311; 106/287.26
[58] Field of Search ........................... 106/287.26, 311

[56] References Cited

U.S. PATENT DOCUMENTS 3,755,191  8/1973  Mottez et al. ...................... 252/364
4,379,000  4/1983  Biggin et al. ........................ 106/311

Primary Examiner—William R. Dixon, Jr.
Assistant Examiner—Alan Wright
Attorney, Agent, or Firm—Oblon, Spivak, McClelland, Maier & Neustadt

[57] ABSTRACT

A $C_{10}$ alcohol mixture for plasticizer, which comprises 2-propylheptanol (hereinafter referred to as "PRH"), an alcohol having a structure of condensation product of n-valeraldehyde and 2-methylbutyraldehyde (hereinafter referred to as "Component A"), an alcohol having a structure of condensation product of n-valeraldehyde and 3-methylbutyraldehyde (hereinafter referred to as "Component B"), an alcohol having a structure of condensation product of n-valeraldehyde and pivalaldehyde (hereinafter referred to as "Component C"), and other $C_{10}$ alcohols (hereinafter referred to as "Component D"), characterized in that the respective components are present in the following molar ratios:

Component A/PRH=0.04-1
Component B/PHR=0.002-0.3
Component C/PRH=0.001-0.3
Component D/PRH≦0.3.

12 Claims, No Drawings

ALCOHOL MIXTURE FOR PLASTICIZER AND METHOD FOR PRODUCING THE SAME

The present invention relates to an alcohol mixture for plasticizer, a method for producing the same and a plasticizer derived from the same.

An alcohol having 10 carbon atoms (hereinafter referred to as "$C_{10}$ alcohol" or decyl alcohol) is prepared by subjecting a $C_4$ olefin to hydroformylation, aldol condensation and hydrogenation, and the alcohol thus prepared is mainly used as a starting material for preparing a plasticizer for vinyl chloride resin.

Thus, the present invention relates to a decyl alcohol mixture having generally excellent properties as a starting material for a plasticizer, a plasticizer prepared therefrom and a method for producing the same.

A decyl alcohol is prepared by hydroformylating a fraction containing 4 carbon atoms obtained in a large amount by thermal cracking or catalytic cracking of hydrocarbon oils (hereinafter referred to as "BB fraction") to obtain valeraldehydes, subjecting the valeraldehydes thus obtained to aldol condensation to obtain decenals, and finally hydrogenating the decenals thus obtained. Butenes in BB fraction include three types of 1-butene, 2-butene and isobutene. Accordingly, valeraldehydes obtained by hydroformylating these butenes include a mixture of n-valeraldehyde (hereinafter referred to as "n-VAD)", 2-methylbutyraldehyde, 3-methylbutyraldehyde and pivalaldehyde (2,2-dimethylpropionaldehyde). Therefore, condensation products of valeraldehydes obtained by the hydroformylation of the BB fraction and their decyl alcohol products generally comprise mixtures of various types of isomers.

U.S. Pat. Nos. 2921089 and 3121051 disclose 2-propylheptanol derived from condensation products of n-valeraldehyde and decyl alcohol derived from cross-aldol condensation products of n-valeraldehyde and 2-methylbutyraldehyde, and also disclose that methods of condensation and hydrogenation may be generally conducted methods, that 2-propylheptanol is excellent as a decyl alcohol for a plasticizer, and that the cross-aldol condensation product is inferior as a starting material for a plasticizer to 2-propylheptanol but it is comparable to 2-propylheptanol if it is used as a mixture with 2-propylheptanol in an amount of up to ten several %.

Von Bernhard et al, Chemiker-Zeitung 99 Jahrgang (1975), Nr11, P452-458 and Japanese Unexamined Patent Publication No. 127335/1980 disclose about oxo reaction of butenes, and also disclose that valeraldehyde can be produced under normal hydroformylation conditions and that n-valeraldehyde can be produced selectively at a higher yield under special hydroformylation conditions.

Japanese Unexamined Patent Publication No. 206537/1983 discloses the composition of valeraldehydes and the condensation conditions for controlling the amount of the cross-aldol condensation product of n-valeraldehyde and 2-methylbutyraldehyde among 2-propylheptanols to less than 20% in order to prepare decyl alcohols having good plasticizer-aptitude from butenes, and also discloses the performance of two-component type alcohol mixture comprising 2-propylheptanol and the cross-aldol condensation product of n-valeraldehyde and 2-methylbutyraldehyde.

BB fraction industrially valuable as a $C_4$ olefin material includes butenes (1-butene, 2-butene and isobutene) as well as $C_3$ hydrocarbons, butadiene, butane or the like, the butene concentration of which is generally about from 40 to 80% by weight.

The BB fraction includes, so to speak, "spent BB fraction" prepared after extracting a substantial amount of butadiene and, so to speak, "spent spent BB fraction" prepared by further removing a part of isobutene. The butene concentration of the former is about from 60 to 90% by weight and that of the latter is about from 70 to 90% by weight.

However, in any case, physical properties of butenes are very similar to each other, and therefore it takes much costs to separate 1-butene, 2-butene and isobutene respectively alone, thus leading to industrial demerits.

It is therefore desirable to prepare decyl alcohols having good plasticizer-aptitude from mixed butenes including 1-butene, 2-butene and isobutene as they are.

It is known that the composition of valeraldehyde product can be controlled to some extents by appropriately selecting reaction conditions and catalysts in the hydroformylation of a $C_4$ olefin mixture. However, there was no method for producing a product without containing undesired specific components, and therefore the product contains all the components including n-valeraldehyde, 2-methylbutyraldehyde, 3-methylbutyraldehyde and pivalaldehyde. Accordingly, the composition of decyl alcohol produced therefrom becomes a mixture of many types of isomers.

It is therefore desired to selectively produce a decyl alcohol mixture comprising isomers having good plasticizer-aptitude from the above four types of valeraldehydes in industrially advantageous manner.

An object of the present invention is to provide a decyl alcohol mixture of isomers having good properties as a starting material for plasticizer.

Another object of the present invention is to provide a method for producing a decyl alcohol mixture of isomers having good plasticizer-aptitude from the above four types of valeraldehydes in industrially advantageous manner.

Still other object of the present invention is to provide a plasticizer having generally excellent properties.

Thus, the present invention, in a broad sense, resides in a $C_{10}$ alcohol mixture for plasticizer, which comprises 2-propylheptanol (hereinafter referred to as "PRH"), an alcohol having a structure of condensation product of n-valeraldehyde and 2-methylbutyraldehyde (hereinafter referred to as "Component A"), an alcohol having a structure of condensation product of n-valeraldehyde and 3-methylbutyraldehyde (hereinafter referred to as "Component B"), an alcohol having a structure of condensation product of n-valeraldehyde and pivalaldehyde (hereinafter referred to as "Component C"), and other $C_{10}$ alcohols (hereinafter referred to as "Component D"), characterized in that the respective components are present in the following molar ratios:

Component A/PRH=0.04-1
Component B/PRH=0.002-0.3
Component C/PRH=0.001-0.3
Component D/PRH≦0.3.

The present invention further resides in a plasticizer obtained by esterifying the above $C_{10}$ alcohol mixture with a carboxylic acid.

The present invention still further resides in a method for producing a $C_{10}$ alcohol mixture for plasticizer, which comprises subjecting butene fraction to hydroformylation, aldol condensation and hydrogenation, characterized in that an aldehyde composition participated in said condensation comprises $C_5$ aldehydes in the following molar ratios, 2-Methylbutyraldehyde/n-VAD=0.02-0.3
3-Methylbutyraldehyde/n-VAD=0.001-0.05
Pivalaldehyde/n-VAD=0.0005-0.05

(wherein n-VAD means n-valeraldehyde) and that the conversion of each $C_5$ aldehyde is at least 90%.

The present invention is described in more detail hereinafter. The $C_{10}$ alcohol mixture of the present invention is characterized in that the above respective Components A to D are present in the following molar ratios:

Component A/PRH=0.04-1
Component B/PRH=0.002-0.3
Component C/PRH=0.001-0.3
Component D/PRH$\leq$0.3.

A method for producing the alcohol for plasticizer of the present invention is not specially limited so long as the above each component is within the above-mentioned composition ranges. For example, the alcohols for plasticizer of the present invention include $C_{10}$ alcohols obtained by hydroformylation and hydrogenation of $C_9$ olefins obtained by trimerization of propylene or copolymerization of olefins including the reaction of $C_4$ olefin with $C_5$ olefin; $C_{10}$ alcohols obtained by subjecting $C_4$ olefins to hydroformylation, aldol condensation and hydrogenation; or an alcohol mixture prepared from these products by adjusting the mixing ratio of each component.

A method for producing a decyl alcohol mixture of the present invention in industrially advantageous manner, which comprises subjecting butene fraction as a $C_4$ olefin to hydroformylation, aldol condensation and hydrogenation, is more concretely explained hereinafter.

"Butene fraction" used as a starting material, includes BB fractions containing butenes as the main component, such as BB fraction obtained by thermal cracking of hydrocarbon oils including naphtha or the like or BB fraction obtained by catalytic cracking (FCC or the like) of hydrocarbon oils including heavy or light oils.

In addition to the above starting materials, spent BB fraction obtained by removing the majority of butadiene from the above-mentioned BB fraction of the thermal cracking or catalytic cracking, spent spent BB fraction obtained by further removing a part of isobutene therefrom and a mixture thereof can also be favorably used.

The alcohol for plasticizer of the present invention is a $C_{10}$ alcohol mixture having the specific composition, and can be obtained by subjecting the above-mentioned butene fraction to hydroformylation, aldol condensation and hydrogenation.

The hydroformylation is carried out in the accordance with a normal method. The hydroformylating conditions are not specially critical, but any of the conventionally known rhodium method and the cobalt method can be used. However, it is economically advantageous that the ratio of $\alpha$-form in the valeraldehyde product is larger. In the case of the rhodium method, any of an organic salt such as rhodium acetate, and an inorganic salt such as rhodium nitrate or a complex such as hydridecarbonyl tris(triphenylphosphine) rhodium and the like can be used as the rhodium source. In the case of the cobalt method, an organic acid salt such as cobalt laurate, an inorganic salt such as cobalt nitrate and a complex such as dicobalt octacarbonyl, hydride cobalt tetracarbonyl or the like can be used.

The reaction pressure is generally from normal pressure to 300 kg/cm$^2$G, the reaction temperature being generally from 50° to 150° C., $H_2$/CO ratio being generally from 1 to 10 by molar ratio and the catalyst concentration being generally from several ppm to several % by weight. Trivalent organophosphorus compounds such as triphenyl phosphine, triphenyl phosphite or the like or their oxides can be used as a ligand to the abovementioned catalyst in a molar ratio of generally from 1 to 1000 to the catalyst.

A solvent may not be used, but may be used if necessary. Any solvent can be used if it dissolves the catalyst and does not have an adverse influence on the reaction. Examples of the solvent include aromatic hydrocarbons such as benzene, toluene, xylene, dodecylbenzene or the like; cycloaliphatic hydrocarbons such as cyclohexane or the like; ethers such as dibutylether, ethylene glycol dimethylether, diethylene glycol diethylether, triethylene glycol dimethylether, tetrahydrofuran or the like; and esters such as diethylphthalate, dioctylphthalate or the like. Aldehydes or alcohols formed in the hydroformylation can also be used as a solvent. High boiling point by products such as polymerization-condensation products of aldehydes can also be used.

The reaction can be carried out by either continuous or batch wise manner.

By distillation, the valeraldehyde products can be recovered and their composition can be controlled.

It is known that the reaction speed of each component of butenes is different from each other in the hydroformylation and that the ratio of $\alpha$-aldehyde and isoaldehyde can be varied to some extent by varying the reaction conditions.

Accordingly, the composition of a valeraldehyde mixture can be controlled to some extent by employing appropriate reaction conditions. Each component of the valeraldehyde mixture has a boiling point difference of 10-20° C., and the composition can be controlled also by normal distillation.

In order to obtain the alcohol mixture for plasticizer of the present invention, the valeraldehyde mixture participated in aldol condensation should preferably have the following molar ratios, 2-Methylbutyraldehyde/n-VAD=0.02-0.3, preferably 0.05-0.3,
3-Methylbutyraldehyde/n-VAD=0.001-0.05, preferably 0.001-0.03, and
Pivalaldehyde/n-VAD=0.0005-0.05, preferably 0.001-0.03.

The aldol condensation is usually carried out by using an alkaline aqueous solution such as sodium hydroxide, potassium hydroxide or the like as a catalyst, but amines also can be used. The reaction temperature is generally from 50° to 150° C, the reaction pressure being generally from normal pressure to several kg/cm$^2$G and the reaction time being from several minutes to several hours. The conversion rate of each component of the valeraldehyde mixture should preferably be about at least 90%, more preferably at least 95%.

The condensation speeds of valeraldehydes other than n-valeraldehyde are relatively slow, and therefore the mutual condensation of valeraldehydes other than n-valeraldehyde or the dimerization of the other valeraldehydes themselves do not substantially occur. However, the cross-aldol condensation with n-valeraldehyde in the above-mentioned $C_5$ aldehyde composition relatively speedily occurs, thereby producing a decenal mixture having the desired composition. The decenal mixture is thereafter subjected to hydrogenation. The hydrogenation can be carried out in usual manner. That is, the hydrogenation is carried out in the presence of a usual hydrogenation catalyst such as Ni, Cr, Cu or the like, under a pressure of from normal pressure to 150 kg/cm$^2$G at a temperature of from 40° to 300° C.

Thereafter, the $C_{10}$ alcohol mixture of the present invention can be obtained by general distillation refining.

The $C_{10}$ alcohol mixture for plasticizer of the present invention comprises not only 2-propylheptanol (PRH) but also an alcohol having a structure of condensation product of n-valeraldehyde and 2-methylbutyraldehyde (Component A):

$$C-C-C-C-C-C-OH \text{ and}$$
with branches C, C-C-C $$C-C-C-C-C-C-C-OH$$
with branches C, C-C-C an alcohol having a structure of condensation product of n-valeraldehyde and 3-methylbutyraldehyde (Component B):

$$C-C-C-C-C-C-OH \text{ and}$$
with branches C, C-C-C $$C-C-C-C-C-C-C-OH$$
with branch C-C, C an alcohol having a structure of condensation product of n-valeraldehyde and pivalaldehyde (Component C):

$$C-C-C-C-C-OH$$
with branches C (top), C, C-C-C and other $C_{10}$ alcohols (Component D)
(in the above chemical structural formulas, every hydrogen atoms bonded to carbon atoms are omitted), the respective components being present in the following molar ratios:

Component A/PRH=0.04-1.0, preferably 0.05-1.0, more preferably 0.1-0.7;
Component B/PRH=0.002-0.3 preferably 0.002-0.3, more preferably 0.002-0.1;
Component C/PRH=0.001-0.3 preferably 0.002-0.3, more preferably 0.002-0.1; and
Component D/PRH≦0.3, preferably not more than 0.1.

The above prepared decyl alcohol mixture is then esterified with phthalic anhydride or the like in the presence of a titanium type catalyst, acidic catalyst (p-toluene sulfonic acid) or the like in usual manner to produce phthalic acid ester usable as a plasticizer. Examples of other plasticizers derived from the $C_{10}$ alcohol mixture of the present invention include aromatic carboxylic acid esters prepared by the esterification reaction of the $C_{10}$ alcohol mixture with aromatic carboxylic acids such as pyromellitic anhydride, trimellitic anhydride or the like, and aliphatic dibasic acid esters prepared by the esterification reaction of the $C_{10}$ alcohol mixture with aliphatic dibasic acids such as adipic acid, azelaic acid, sebacic acid or the like.

It is known that decyl alcohol containing 2-propylheptanol as the main component is generally superior in heat resistance to widely used 2-ethylhexanol for plasticizer, but is inferior in electric resistance and plasticizing efficiency.

The performance of plasticizer should be totally evaluated in view of
(1) Plasticizing efficiency (100% modulus)
(2) Evaporation loss (heat resistance)
(3) Cold flex temperature (cold resistance)
(4) Kerosine extraction (oil resistance) and
(5) Electric resistance (electrical insulating properties)

It should not be evaluated from single property, for example, heat resistance only.

Among the above properties, some properties, for example, properties (2) and (5) tend to be contrary each other, and are complicated. The decyl alcohol mixture prepared by the present invention include structures of 2- or 3-methylbutyraldehyde and pivalaldehyde in a small amount, thus providing an alcohol for plasticizer having generally excellent properties.

[EXAMPLE]

Now, the present invention will be described in detail with reference to Examples. However, it should be understood that the present invention is by no means restricted to such specific Examples.

REFERENCE EXAMPLE 1

(1) Synthesis of 2-propylheptanol

Commercially available genuine n-valeraldehyde was subjected to condensation reaction. The condensation was carried out batch wise for 30 minutes at 95° C. under normal pressure in the presence of 3% sodium hydroxide aqueous solution/n-valeraldehyde=1 (weight ratio)

The conversion of n-valeraldehyde was 99.9%.

Decenal obtained after liquid-liquid separation was hydrogenated in the presence of a nickel type solid catalyst. The hydrogenation was batch wise conducted for 3.0 hours at 100° C. under pressure of 100 kg/cm$^2$G in the presence of the catalyst/decenal=0.1 (weight ratio). The conversion of decenal was 99.9%.

The crude 2-propylheptanol thus obtained was rectified by a glass-made Oldershow type distillation tower having 30 plates, thereby obtaining the refined 2-propylheptanol under the conditions of initial cut 1%, main fraction 96% and ending cut 4%.

(2) Synthesis of plasticizer and evaluation thereof

2-Propylheptanol obtained in the above step (1) and phthalic anhydride were esterified in usual manner to prepare a plasticizer.

The plasticizer thus prepared was mixed with vinyl chloride resin in a ratio of plasticizer/vinyl chloride resin=67/100 (weight ratio) in usual manner to prepare a soft type vinyl chloride resin, and the vinyl chloride resin was subjected to various tests by a usual method to evaluate various properties of the resin.

The test results are shown in Table 1. The same test results with regard to commonly used plasticizer, di-2-ethylhexylphthalate (DOP) are also shown in Table 1.

EXAMPLE 1

Spent spent BB fraction having the following composition prepared by removing the majority of butadiene and isobutene from BB fraction produced from a naphtha cracker was continuously hydroformylated under the following conditions.

| Composition: | 1-butene | 43 wt % |
|---|---|---|
| | 2-butene | 22 |
| | isobutene | 4 |
| | butadiene | 1.3 |
| | $C_3$'s | 0.3 |
| | others | 29.4 |
| Reaction Conditions: | Total pressure 7 kg/cm$^2$G | |
| | Oxo gas partial pressure 4 kg/cm$^2$G ($H_2$/CO = 1), | |
| | Reaction temperature: 100° C. | |
| Catalyst liquor | Rhodium catalyst (concentration 300 ppm (calculation as Rh atom)) | |
| | Triphenylphosphine (concentration 30% by weight) | |
| | Solvent: xylene | |
| Feed/catalyst liquor = 10 (weight ratio) | | |
| Reactor residence time: 2.0 hours | | |

After depressurizing the reaction liquor, the valeraldehyde mixture thus produced was recovered by distillation in substantially total amount, the molar ratios of which were as follows:

2-Methylbutyraldehyde/n-VAD=0.1
3-Methylbutyraldehyde/n-VAD=0.02
Pivalaldehyde/n-VAD=0.01

The resultant valeraldehyde mixture, as it is, was then subjected to condensation reaction in a 10 l autoclave for 1.5 hours at 95° C. under normal pressure in the presence of 3% sodium hydroxide aqueous solution/aldehyde=1 (weight ratio).

The conversion of each aldehyde was as follows:

| n-Valeraldehyde | 99.9% |
|---|---|
| 2-Methylbutyraldehyde | 99.8 |
| 3-Methylbutyraldehyde | 99.8 |
| Pivalaldehyde | 98.2 |

The decenal mixture thus obtained was hydrogenated in the same manner as in Reference Example 1 to obtain a decyl alcohol mixture, and the resultant decyl alcohol mixture was refined. Various properties of a plasticizer prepared from this decyl alcohol mixture were evaluated and the results are shown in Table 1.

The composition of this decyl alcohol mixture was analyzed by capillary gaschromatography, and had the following molar ratio as a result.

Component A/PRH=0.22
Component B/PRH=0.045
Component C/PRH=0.022
Component D/PRH=0.01

EXAMPLE 2

The same starting material as used in Example 1 was hydroformylated in the same manner as in Example 1, except that the total pressure was 18 kg/cm$^2$G and the oxo gas partial pressure was 15 kg/cm$^2$ ($H_2$/CO=1). The molar ratio of the valeraldehyde mixture thus produced was as follows:

2-Methylbutyraldehyde/n-VAD=0.5
3-Methylbutyraldehyde/n-VAD=0.1
Pivalaldehyde/n-VAD=0.1

The resultant valeraldehyde mixture was rectified by a glass-made Oldershow type distillation tower having 90 plates to distill out a part of the respective pivalaldehyde, 2-methylbutyraldehyde and 3-methylbutyraldehyde, thereby obtaining a mixture having the following molar ratio.

2-Methylbutyraldehyde/n-VAD=0.2
3-MethylbutYraldehyde/n-VAD=0.03
Pivalaldehyde/n-VAD=0.02

The resultant mixture having the above molar ratio was subjected to condensation under the same conditions as in Example 1.

| n-Valeraldehyde | 99.9% |
|---|---|
| 2-Methylbutyraldehyde | 99.0 |
| 3-Methylbutyraldehyde | 98.5 |
| Pivalaldehyde | 98.0 |

The decenal mixture thus obtained was hydrogenated in the same manner as in Reference Example 1 to obtain a decyl alcohol mixture, and the resultant decyl alcohol mixture was refined. Various properties of a plasticizer prepared from this decyl alcohol mixture were evaluated and the results are shown in Table 1.

The composition of this decyl alcohol mixture was analyzed by capillary gaschromatography, and had the following molar ratio as a result.

Component A/PRH=0.48
Component B/PRH=0.073
Component C/PRH=0.05
Component D/PRH=0.02

EXAMPLE 3

Spent BB fraction having the following composition prepared by removing butadiene from BB fraction produced from a naphtha cracker was hydroformylated to produce a valeraldehyde mixture under the same conditions as in Example 1, except that the reaction temperature was 110° C.

The composition of the starting material:

| 1-butene | 24.3 wt % |
|---|---|
| 2-butene | 13.1 |
| isobutene | 51.5 |
| butadiene | 0.02 |
| $C_3$'s | 0.15 |
| others | 10.93 |

The molar ratios of the valeraldehyde mixture thus produced were as follows:

2-Methylbutyraldehyde/n-VAD = 0.3
3-Methylbutyraldehyde/n-VAD = 0.03
Pivalaldehyde/n-VAD = 0.04

The resultant valeraldehyde mixture was then subjected to condensation reaction under the same conditions as in Example 1, except that the concentration of sodium hydroxide aqueous solution was made 5%.

The conversion of each aldehyde was as follows:

| n-Valeraldehyde | 99.9% |
|---|---|
| 2-Methylbutyraldehyde | 99.1 |
| 3-Methylbutyraldehyde | 98.3 |
| Pivalaldehyde | 97.8 |

The decenal mixture thus obtained was hydrogenated in the same manner as in Example 1 to obtain a decyl alcohol mixture, and the resultant decyl alcohol mixture was refined. Various properties of a plasticizer prepared from this decyl alcohol mixture were evaluated and the results are shown in Table 1.

The composition of this decyl alcohol mixture was analyzed by capillary gaschromatography, and had the following molar ratio as a result.
Component A/PRH=0.93
Component B/PRH=0.09
Component C/PRH=0.12
Component D/PRH=0.03

REFERENCE EXAMPLE 2

The valeraldehyde mixture (before rectified) obtained by the hydroformylation in Example 2 was subjected to condensation, hydrogenation and refining to produce a decyl alcohol mixture. Various properties of a plasticizer prepared from this decyl alcohol mixture were evaluated and the results are shown in Table 1.

The conversion of each aldehyde was as follows:

| n-Valeraldehyde | 99.9% |
|---|---|
| 2-Methylbutyraldehyde | 92.2 |
| 3-Methylbutyraldehyde | 93.5 |
| Pivalaldehyde | 91.8 |

The composition of the decyl alcohol mixture had the following molar ratio as a result.
Component A/PRH=1.3
Component B/PRH=0.3
Component C/PRH=0.3
Component D/PRH=0.03

REFERENCE EXAMPLE 3

A decyl alcohol mixture was prepared in the same manner as in Reference Example 1, except that a commercially available mixture of n-valeraldehyde and 2-methylbutyraldehyde (1:0.1 weight ratio) was used as a starting material for condensation. Various properties of a plasticizer prepared from this decyl alcohol mixture were evaluated and the results are shown in Table 1.

The conversion of each valeraldehyde was as follows:

| n-Valeraldehyde | 99.9% |
|---|---|
| 2-Methylbutyraldehyde | 99.2 |

The composition of the decyl alcohol mixture had the following molar ratio.
Component A/PRH=0.22
Component B/PRH=0
Component C/PRH=0
Component D/PRH=0.01

REFERENCE EXAMPLE 4

A decyl alcohol mixture was prepared in the same manner as in Reference Example 1, except that a commercially available mixture of n-valeraldehyde: 2-methylbutyraldehyde: 3-methylbutyraldehyde (1:0.3:0.02 weight ratio) was used as a starting material for condensation and hydrogenation. Various properties of a plasticizer prepared from this decyl alcohol mixture were evaluated and the results are shown in Table 1.

The conversion of each valeraldehyde was as follows:

| n-Valeraldehyde | 99.9% |
|---|---|
| 2-Methylbutyraldehyde | 99 |
| 3-Methylbutyraldehyde | 98.5 |

The composition of the decyl alcohol mixture had the following molar ratio.
Component A/PRH=0.88
Component B/PRH=0.058
Component C/PRH=0
Component D/PRH=0.03

TABLE 1

| | | Reference Example 1 | Reference Example 1 (DOP) | Example 1 | Example 2 | Example 3 | Reference Example 2 | Reference Example 3 | Reference Example 4 |
|---|---|---|---|---|---|---|---|---|---|
| Composition of VAD participated in condensation (molar ratio) | 2-Methylbutyraldehyde/n-VAD | n-VAD genuine | | 0.1 | 0.2 | 0.3 | 0.5 | 0.1 | 0.3 |
| | 3-Methylbutyraldehyde/n-VAD | | | 0.02 | 0.03 | 0.03 | 0.1 | 0 | 0.02 |
| | Pivalaldehyde/n-VAD | | | 0.01 | 0.02 | 0.04 | 0.1 | 0 | 0 |
| Alcohol composition (molar ratio) | Component A/PRH | PRH | 2-Ethylhexanol | 0.22 | 0.48 | 0.93 | 1.3 | 0.22 | 0.88 |
| | Component B/PRH | | | 0.045 | 0.073 | 0.09 | 0.3 | 0 | 0.058 |
| | Component C/PRH | | | 0.022 | 0.05 | 0.12 | 0.3 | 0 | 0 |
| | Component D/PRH | | | 0.01 | 0.02 | 0.03 | 0.03 | 0.01 | 0.03 |
| Evaluation of plasticizer properties | 100% Modulus (kg/cm$^2$) | 77 | 64 | 68 | 68 | 65 | 70 | 76 | 68 |
| | Evaporation loss (%) (87° C.) 1 day | 0.9 | 4.2 | 0.9 | 1.2 | 1.3 | 3.8 | 1.1 | 1.1 |
| | Evaporation loss (%) (87° C.) 6 days | 4.5 | 19.8 | 4.9 | 5.8 | 5.7 | 18.9 | 5.8 | 5.0 |

TABLE 1-continued

| | Reference Example 1 | Reference Example 1 (DOP) | Example 1 | Example 2 | Example 3 | Reference Example 2 | Reference Example 3 | Reference Example 4 |
|---|---|---|---|---|---|---|---|---|
| Cold flex temperature (°C.) | −39 | −38 | −39 | −37 | −36 | −30 | −37 | −38 |
| Kerosine extraction (%) (23° C. × 1 day) | 61 | 44.6 | 42.1 | 40.3 | 38.2 | 53 | 59 | 60 |
| Electric resistance (× $10^{12}$ Ω · m) | 6.3 | 12.5 | 13.5 | 15.3 | 18.4 | 18.2 | 6.9 | 7.4 |

EXAMPLE 4

Spent spent BB fraction having the following composition prepared by removing the majority of butadiene and isobutene from BB fraction produced from a naphtha cracker was continuously hydroformylated under the following conditions.

| Composition: | 1-butene | 43 wt % |
|---|---|---|
| | 2-butene | 22 |
| | isobutene | 0.71 |
| | butadiene | 1.3 |
| | $C_3$'s | 0.3 |
| | others | 32.7 |
| Reaction Conditions: | Total pressure 9 kg/cm$^2$G | |
| | Oxo gas partial pressure 4 kg/cm$^2$G ($H_2$/CO = 1), | |
| | Reaction temperature: 100° C. | |
| Catalyst liquor | Rhodium catalyst (concentration 300 ppm (calculation as Rh atom)) Triphenylphosphine (concentration 30% by weight) Solvent: xylene | |
| Feed/catalyst liquor = 10 (weight ratio) | | |
| Reactor residence time: 2.0 hours | | |

After depressurizing the reaction liquor, the valeraldehyde mixture thus produced was recovered by distillation in substantially total amount, the molar ratios of which were as follows:
2-Methylbutyraldehyde/n-VAD=0.1
3-Methylbutyraldehyde/n-VAD=0.0030
Pivalaldehyde/n-VAD=0.0048

The resultant valeraldehyde mixture, as it is, was then subjected to condensation reaction in a 10 l autoclave for 1.7 hours at 95° C. under normal pressure in the presence of 3% sodium hydroxide aqueous solution/aldehyde=1 (weight ratio).

The conversion of each aldehyde was as follows:

| n-Valeraldehyde | 99.9% |
|---|---|
| 2-Methylbutyraldehyde | 99.8 |
| 3-Methylbutyraldehyde | 97.5 |
| Pivalaldehyde | 99.4 |

The decenal mixture thus obtained was hydrogenated in the same manner as in Reference Example 1 to obtain a decyl alcohol mixture, and the resultant decyl alcohol mixture was refined. Various properties of a plasticizer prepared from this decyl alcohol mixture were evaluated and the results are shown in Table 2.

The composition of this decyl alcohol mixture was analyzed by capillary gaschromatography, and had the following molar ratio as a result.
Component A/PRH=0.22
Component B/PRH=0.004
Component C/PRH=0.011
Component D/PRH=0.01

EXAMPLE 5

Spent spent BB fraction having the following composition prepared by removing the majority of butadiene and isobutene from BB fraction produced from a naphtha cracker was continuously hydroformylated under the following conditions.

| Composition: | 1-butene | 43 wt % |
|---|---|---|
| | 2-butene | 22 |
| | isobutene | 0.68 |
| | butadiene | 1.3 |
| | $C_3$'s | 0.3 |
| | others | 32.7 |
| Reaction Conditions: | Total pressure 8 kg/cm$^2$G | |
| | Oxo gas partial pressure 4 kg/cm$^2$G ($H_2$/CO = 1), | |
| Reaction temperature: | 100° C. | |
| Catalyst liquor | Rhodium catalyst (concentration 300 ppm (calculation as Rh atom)) Triphenylphosphine (concentration 30% by weight) Solvent: xylene | |
| Feed/catalyst liquor = 10 (weight ratio) | | |
| Reactor residence time: 2.0 hours | | |

After depressurizing the reaction liquor, the valeraldehyde mixture thus produced was recovered by distillation in substantially total amount, the molar ratios of which were as follows:
2-Methylbutyraldehyde/n-VAD=0.1
3-Methylbutyraldehyde/n-VAD=0.003
Pivalaldehyde/n-VAD=0.0026

The resultant valeraldehyde mixture, as it is, was then subjected to condensation reaction in a 10 l autoclave for 1.8 hours at 95° C. under normal pressure in the presence of 3% sodium hydroxide aqueous solution/aldehyde=1 (weight ratio).

The conversion of each aldehyde was as follows:

| n-Valeraldehyde | 99.9% |
|---|---|
| 2-Methylbutyraldehyde | 99.8 |
| 3-Methylbutyraldehyde | 97.5 |
| Pivalaldehyde | 99.4 |

The decenal mixture thus obtained was hydrogenated in the same manner as in Reference Example 1 to obtain a decyl alcohol mixture, and the resultant decyl alcohol mixture was refined. Various properties of a plasticizer prepared from this decyl alcohol mixture were evaluated and the results are shown in Table 2.

The composition of this decyl alcohol mixture was analyzed by capillary gaschromatography, and had the following molar ratio as a result.

Component A/PRH=0.22
Component B/PRH=0.004
Component C/PRH=0.006
Component D/PRH=0.01

EXAMPLE 6

Spent spent BB fraction having the following composition prepared by removing the majority of butadiene and isobutene from BB fraction produced from a naphtha cracker was continuously hydroformylated under the following conditions.

| Composition: | 1-butene | 57.9 wt % |
| --- | --- | --- |
| | 2-butene | 7.1 |
| | isobutene | 0.68 |
| | butadiene | 1.3 |
| | $C_3$'s | 0.3 |
| | others | 32.7 |
| Reaction Conditions: | Total pressure 7 kg/cm$^2$G | |
| | Oxo gas partial pressure 4 kg/cm$^2$G ($H_2$/CO = 1), | |
| | Reaction temperature: 100° C. | |
| Catalyst liquor | Rhodium catalyst (concentration 300 ppm (calculation as Rh atom)) | |
| | Triphenylphosphine (concentration 30% by weight) | |
| | Solvent: xylene | |
| Feed/catalyst liquor = 10 (weight ratio) | | |
| Reactor residence time: 2.0 hours | | |

After depressurizing the reaction liquor, the valeraldehyde mixture thus produced was recovered by distillation in substantially total amount, the molar ratios of which were as follows:

2-Methylbutyraldehyde/n-VAD=0.04
3-Methylbutyraldehyde/n-VAD=0.0025
Pivalaldehyde/n-VAD=0.0025

The resultant valeraldehyde mixture, as it is, was then subjected to condensation reaction in a 10 l autoclave for 1.8 hours at 95° C. under normal pressure in the presence of 3% sodium hydroxide aqueous solution/aldehyde=1 (weight ratio).

The conversion of each aldehyde was as follows:

| n-Valeraldehyde | 99.9% |
| --- | --- |
| 2-Methylbutyraldehyde | 99.8 |
| 3-Methylbutyraldehyde | 97.0 |
| Pivalaldehyde | 98.2 |

The decenal mixture thus obtained was hydrogenated in the same manner as in Reference Example 1 to obtain a decyl alcohol mixture, and the resultant decyl alcohol mixture was refined. Various properties of a plasticizer prepared from this decyl alcohol mixture were evaluated and the results are shown in Table 2.

The composition of this decyl alcohol mixture was analyzed by capillary gaschromatography, and had the following molar ratio as a result.

Component A/PRH=0.08
Component B/PRH=0.004
Component C/PRH=0.006
Component D/PRH=0.01

EXAMPLE 7

Spent spent BB fraction having the following composition prepared by removing the majority of butadiene and isobutene from BB fraction produced from a naphtha cracker was continuously hydroformylated under the following conditions.

| Composition: | 1-butene | 59 wt % |
| --- | --- | --- |
| | 2-butene | 6.0 |
| | isobutene | 1.2 |
| | butadiene | 1.3 |
| | $C_3$'s | 0.3 |
| | others | 32.2 |
| Reaction Conditions: | Total pressure 5 kg/cm$^2$G | |
| | Oxo gas partial pressure 4 kg/cm$^2$G ($H_2$/CO = 1), | |
| | Reaction temperature: 100° C. | |
| Catalyst liquor | Rhodium catalyst (concentration 300 ppm (calculation as Rh atom)) | |
| | Triphenylphosphine (concentration 30% by weight) | |
| | Solvent: xylene | |
| Feed/catalyst liquor = 10 (weight ratio) | | |
| Reactor residence time: 2.0 hours | | |

After depressurizing the reaction liquor, the valeraldehyde mixture thus produced was recovered by distillation in substantially total amount, the molar ratios of which were as follows:

2-Methylbutyraldehyde/n-VAD=0.03
3-Methylbutyraldehyde/n-VAD=0.005
Pivalaldehyde/n-VAD=0.0014

The resultant valeraldehyde mixture, as it is, was then subjected to condensation reaction in a 10 l autoclave for 1.8 hours at 95° C. under normal pressure in the presence of 3% sodium hydroxide aqueous solution/aldehyde=1 (weight ratio).

The conversion of each aldehyde was as follows:

| n-Valeraldehyde | 99.9% |
| --- | --- |
| 2-Methylbutyraldehyde | 99.8 |
| 3-Methylbutyraldehyde | 99.8 |
| Pivalaldehyde | 98.2 |

The decenal mixture thus obtained was hydrogenated in the same manner as in Reference Example 1 to obtain a decyl alcohol mixture, and the resultant decyl alcohol mixture was refined. Various properties of a plasticizer prepared from this decyl alcohol mixture were evaluated and the results are shown in Table 2.

The composition of this decyl alcohol mixture was analyzed by capillary gaschromatography, and had the following molar ratio as a result.

Component A/PRH=0.06
Component B/PRH=0.01
Component C/PRH=0.003
Component D/PRH=0.001

TABLE 2

| | | Example 4 | Example 5 | Example 6 | Example 7 |
| --- | --- | --- | --- | --- | --- |
| Composition of VAD participated in condensation (molar ratio) | 2-Methylbutyraldehyde/n-VAD | 0.1 | 0.1 | 0.04 | 0.03 |
| | 3-Methylbutyraldehyde/n-VAD | 0.0030 | 0.0030 | 0.0025 | 0.0050 |
| | Pivalaldehyde/n-VAD | 0.0048 | 0.0026 | 0.0025 | 0.0014 |
| Alcohol | Component A/ | 0.22 | 0.22 | 0.08 | 0.06 |

TABLE 2-continued

|  |  | Example 4 | Example 5 | Example 6 | Example 7 |
|---|---|---|---|---|---|
| composition (molar ratio) | PRH | | | | |
| | Component B/PRH | 0.004 | 0.004 | 0.004 | 0.01 |
| | Component C/PRH | 0.011 | 0.006 | 0.006 | 0.003 |
| | Component D/PRH | 0.01 | 0.01 | 0.01 | 0.001 |
| Evaluation of plasticizer properties | 100% Modulus (kg/cm$^2$) | 72 | 70 | 70 | 69 |
| | Evaporation loss (%) (87° C.) 1 day | 0.9 | 0.95 | 0.9 | 0.85 |
| | Evaporation loss (%) (87° C.) 6 days | 5.0 | 4.9 | 5.1 | 4.9 |
| | Cold flex temperature (°C.) | −39 | −39 | −40 | −40 |
| | Kerosine extraction (%) (23° C. × 1 day) | 45.1 | 45.0 | 45.8 | 46.2 |
| | Electric resistance (× 10$^{12}$ Ω · m) | 13.2 | 10.9 | 11.0 | 9.2 |

REFERENCE EXAMPLE 5

A plasticizer was prepared in the same manner as in Reference Example 1, except that the esterification in the step (2) was carried out by using adipic acid in place of phthalic anhydride.

The plasticizer thus prepared was then mixed with vinyl chloride resin in a ratio of plasticizer/vinyl chloride resin=43/100 (weight ratio) in usual manner to prepare a soft type vinyl chloride resin, and the vinyl chloride resin was subjected to various tests by a usual method to evaluate various properties of the resin.

The test results are shown in Table 3. The same test results with regard to commonly used plasticizer, di-2-ethylhexyladipate (DOA) are also shown in Table 3.

EXAMPLE 8

A plasticizer was prepared by esterifying the decyl alcohol mixture produced in Example 1 with adipic acid as used in Reference Example 5. Various properties of the plasticizer thus prepared were evaluated in the same manner as above, and the results are shown in the following Table 3.

EXAMPLE 9

A plasticizer was prepared by esterifying the decyl alcohol mixture produced in Example 4 with adipic acid as used in Example 8. Various properties of the plasticizer thus prepared were evaluated in the same manner as above, and the results are shown in the following Table 3.

REFERENCE EXAMPLE 6

A plasticizer was prepared by esterifying the decyl alcohol mixture produced in Reference Example 2 with adipic acid as used in Example 8. Various properties of the plasticizer thus prepared were evaluated in the same manner as above, and the results are shown in the following Table 3.

TABLE 3

|  |  | Reference Example 5 | Reference Example 5 (DOA) | Example 8 | Example 9 | Reference Example 6 |
|---|---|---|---|---|---|---|
| Composition of VAD participated in condensation (molar ratio) | 2-Methylbutyraldehyde/n-VAD | n-VAD genuine | | 0.1 | 0.1 | 0.5 |
| | 3-Methylbutyraldehyde/n-VAD | | | 0.02 | 0.0030 | 0.1 |
| | Pivalaldehyde/n-VAD | | | 0.01 | 0.0048 | 0.1 |
| Alcohol composition (molar ratio) | A Component/PRH | PRH | 2-Ethylhexanol | 0.22 | 0.22 | 1.3 |
| | B Component/PRH | | | 0.045 | 0.004 | 0.3 |
| | Component C/PRH | | | 0.022 | 0.011 | 0.3 |
| | Component D/PRH | | | 0.01 | 0.01 | 0.3 |
| Evaluation of plasticizer properties | 100% Modulus (kg/cm$^2$) | 129 | 85 | 87 | 89 | 113 |
| | Evaporation loss (%) (87° C.) 1 day | 2.3 | 14.0 | 2.1 | 2.0 | 10.9 |
| | Evaporation loss (%) (87° C.) 6 days | 12.7 | 72.8 | 12.5 | 12.9 | 60.7 |
| | Cold flex temperature (°C.) | −43 | −46 | −44 | −45 | −39 |
| | Kerosine extraction (%) (23° C. × 1 day) | 65.0 | 67.1 | 59.1 | 62.3 | 72.4 |
| | Electric | 1.9 | 3.5 | 5.1 | 4.4 | 10.1 |

TABLE 3-continued

| | Reference Example 5 | Reference Example 5 (DOA) | Example 8 | Example 9 | Reference Example 6 |
|---|---|---|---|---|---|
| resistance ($\times 10^{10}$ Ω·m) | | | | | |

As mentioned above, alcohol having generally excellent properties as a starting material for plasticizer can be prepared in accordance with the method of the present invention.

I claim:

1. A $C_{10}$ alcohol mixture for plasticizer, which comprises 2-propylheptanol (hereinafter referred to as "PRH"), an alcohol having a structure of condensation product of n-valeraldehyde and 2-methylbutyraldehyde (hereinafter referred to as "Component A"), an alcohol having a structure of condensation product of n-valeraldehyde and 3-methylbutyraldehyde (hereinafter referred to as "Component B"), an alcohol having a structure of condensation product of n-valeraldehyde and pivalaldehyde (hereinafter referred to as "Component C"), and other $C_{10}$ alcohols (hereinafter referred to as "Component D"), characterized in that the respective components are present in the following molar ratios:
Component A/PRH=0.04-1.0
Component B/PRH=0.002-0.3
Component C/PRH=0.001-0.3
Component D/PRH≦0.3.

2. The $C_{10}$ alcohol mixture for plasticizer according to claim 1, wherein the molar ratios of the respective components are:
Component A/PRH=0.05-1.0
Component B/PRH=0.002-0.3
Component C/PRH=0.002-0.3
Component D/PRH≦0.1.

3. The $C_{10}$ alcohol mixture for plasticizer according to claim 1, wherein said $C_{10}$ alcohol mixture is obtained by subjecting butene fraction to hydroformylation, aldol condensation and hydrogenation.

4. A plasticizer obtained by esterifying a carboxylic acid with a $C_{10}$ alcohol mixture which comprises 2-propylheptanol (hereinafter referred to as "PRH"), an alcohol having a structure of condensation product of n-valeraldehyde and 2-methylbutyraldehyde (hereinafter referred to as "Component A"), an alcohol having a structure of condensation product of n-valeraldehyde and 3-methylbutyraldehyde (hereinafter referred to as "Component B"), an alcohol having a structure of condensation product of n-valeraldehyde and pivalaldehyde (hereinafter referred to as "Component C"), and other $C_{10}$ alcohols (hereinafter referred to as "Component D"), wherein the respective components are present in the following molar ratios:
Component A/PRH=0.04-1
Component B/PRH=0.002-0.3
Component C/PRH=0.001-0.3
Component D/PRH≦=0.3.

5. The plasticizer according to claim 4, wherein the molar ratios of the respective components in said $C_{10}$ alcohol mixture are:
Component A/PRH=0.05-1.0
Component B/PRH=0.002-0.3
Component C/PRH=0.002-0.3
Component D/PRH≦=0.1.

6. The plasticizer according to claim 4, wherein said carboxylic acid is at least one selected from the group consisting of phthalic acid, aromatic carboxylic acid and aliphatic dibasic acid.

7. A method for producing a $C_{10}$ alcohol mixture for plasticizer, which comprises subjecting butene fraction to hydroformylation, aldol condensation and hydrogenation, characterized in that an aldehyde composition participated in said condensation comprises $C_5$ aldehydes in the following molar ratios,
2-Methylbutyraldehyde/n-VAD=0.02-0.3
3-Methylbutyraldehyde/n-VAD=0.001-0.05
Pivalaldehyde/n-VAD=0.0005-0.05
(wherein n-VAD means n-valeraldehyde) and that the conversion of each $C_5$ aldehyde is at least 90%.

8. The method according to claim 7, wherein said butene fraction is selected from the group consisting of BB fraction obtained by thermal cracking of hydrocarbon oil and BB fraction obtained by catalytic cracking of hydrocarbon oil.

9. The method according to claim 7, wherein said hydroformylation is carried out in the presence of a rhodium catalyst.

10. The method according to claim 7, wherein said aldol condensation is carried out in the presence of an alkali catalyst.

11. The method according to claim 7, wherein said aldehyde composition participated in said condensation comprises $C_5$ aldehydes in the following molar ratios,
2-Methylbutyraldehyde/n-VAD=0.05-0.3
3-Methylbutyraldehyde/n-VAD=0.001-0.03
Pivalaldehyde/n-VAD=0.001-0.03
(wherein n-VAD means n-valeraldehyde).

12. The method according to claim 7, wherein the conversion of each $C_5$ aldehyde in the condensation is at least 95%.

* * * * *